United States Patent [19]
Matay

[11] Patent Number: 4,567,747
[45] Date of Patent: Feb. 4, 1986

[54] SELF-CALIBRATION SYSTEM FOR ULTRASONIC INSPECTION APPARATUS

[75] Inventor: Istvan M. Matay, North Royalton, Ohio

[73] Assignee: TRW Inc., Cleveland, Ohio

[21] Appl. No.: 571,317

[22] Filed: Jan. 16, 1984

[51] Int. Cl.$^4$ ............................................. G01N 29/00
[52] U.S. Cl. ................................... 73/1 DV; 73/598; 73/622; 367/13
[58] Field of Search ............ 73/1 DV, 597, 598, 622; 367/13

[56] References Cited
U.S. PATENT DOCUMENTS

| | | | |
|---|---|---|---|
| 3,512,400 | 5/1970 | Lynnworth | 73/598 |
| 4,121,467 | 10/1978 | Gerhart | 73/597 |
| 4,398,421 | 8/1983 | White | 73/597 |
| 4,434,660 | 3/1984 | Michaels et al. | 73/622 |

Primary Examiner—S. Leon Bashore
Assistant Examiner—Andrew J. Anderson
Attorney, Agent, or Firm—D. G. Blackhurst; S. L. Goldstein

[57] ABSTRACT

A tubular workpiece (10) undergoes axial and rotational movement relative to a collar (12) filled with an acoustically coupling medium (14). Longitudinal waves are emitted into the coupling medium and the workpiece from a first transducer (22) and acoustic echoes are received thereby. From the coupling medium travel times between the transducer and the surface of the workpiece, a contour reconstruction apparatus (58) reconstructs the peripheral contour of the workpiece. The workpiece travel times are stored in a memory (92) until the longitudinal velocity of the acoustic wave in the workpiece is determined. Transducers (24, 26) emit and detect a Rayleigh wave which travels around the workpiece circumference. A divider (80) divides the workpiece circumference as determined by the contour reconstruction apparatus by the Rayleigh wave travel time to determine the Rayleigh wave acoustic velocity. A multiplier (82) multiplies the Rayleigh wave velocity by a preselected Rayleigh wave to longitudinal wave ratio to determine the velocity of the longitudinal wave in the workpiece. A second multiplier (100) multiplies the stored longitudinal wave travel times by the longitudinal wave velocity to determine the thickness of the workpiece and the depth of any acoustically reflective flaws.

19 Claims, 3 Drawing Figures

SELF-CALIBRATION SYSTEM FOR ULTRASONIC INSPECTION APPARATUS

BACKGROUND OF THE INVENTION

The present invention pertains to the art of acoustics, particularly ultrasonic inspection of workpieces. The present invention finds particular application in the inspection of cylindrical, tubular goods to detect flaws, measure wall thickness, and monitor other physical properties. It is to be appreciated, however, that the invention finds further application in the inspection of other workpieces of various sizes and shapes for the above and other purposes.

Heretofore, various inspection systems have been used to inspect pipes and other tubular goods. These prior art inspection systems have included X-radiation inspection systems in which variations in the amount of X-radiation passing through the pipe indicated areas of wall thickness, flaws, and the like. The prior art also included magnetic flux leakage inspection systems in which variations in a magnetic flux leakage field indicated flaws or other non-uniformities in metal tubing. The X-radiation and magnetic flux leakage type tubing inspection systems tended to provide a relatively coarse examination of the tubular product. Once a flaw or thin spot was detected, it was commonly re-examined with a hand held ultrasonic inspection apparatus. Commonly, the hand held ultrasonic apparatus was calibrated by physically measuring the wall thickness in a convenient area with a mechanical gauge, such as a micrometer or the like. The ultrasonic apparatus was then operated to transmit a longitudinal wave through the measured wall thickness. An ultrasonic wave travel time in which the wave traversed the measured thickness is directly proportional to the thickness. The conversion of the travel time to thickness was adjusted or calibrated such that the ultrasonically measured thickness matched the mechanically gauged thickness.

One of the problems encountered with ultrasonics in measuring dimensions and other physical properties is that the velocity of the ultrasonic wave varies significantly with subtle differences in the physical structure of the workpiece. The acoustic wave velocities vary with such physical properties as elastic moduli and density which, in turn, may be a function of metallurgical composition and manufacturing process variations, and the like. For example, the acoustic velocity of ultrasonic waves in steel tubing will vary with such factors as the temperature to which the steel was heated at the mill, the rate at which the steel was cooled, the steel composition, impurities and variations in the steel components, and the like. It has been found that the acoustic velocity of ultrasonic waves in steel tubing meeting common specifications varies as much as 400% from one mill to another. Further, the acoustic velocity varies with the batch of steel from which the tubing was manufactured, and may even vary within a single workpiece. Accordingly, in order to automate and insure accurate measurements, frequent recalibration of the ultrasonic instrument is necessary to compensate for acoustic velocity variations in the product under examination.

The present invention contemplates a new and improved acoustic inspection system which overcomes the above referenced problems and others.

SUMMARY OF THE INVENTION

In accordance with the present invention, an acoustic inspection method and system is advantageously provided which is recalibrated regularly as a function of an acoustically measured physical distance or dimension.

In accordance with one aspect of the present invention, there is provided a method of acoustically inspecting workpieces. A preselected physical calibration distance is determined along the workpiece being inspected. A first travel time in which a first acoustic wave travels the calibration distance is measured and a calibration acoustic velocity is determined from the calibration distance and the first travel time. A second travel time is measured in which a second acoustic wave travels through a portion of the workpiece to be inspected. An inspection distance is then determined from the calibration acoustic velocity and the second travel time.

In accordance with a more limited aspect of the invention, the calibration distance is determined acoustically by measuring coupling medium travel times in which acoustic waves travel through an acoustic coupling medium that contacts the workpiece along the calibration distance.

In accordance with another aspect of the present invention, there is provided an acoustic inspection system. A calibration distance determining means determines a preselected physical calibration distance along the workpiece being inspected. A first travel time measuring means measures a first travel time in which a first acoustic wave travels the calibration distance. A calibration acoustic velocity determining means determines a calibration acoustic velocity from the calibration distance and the calibration travel time. A workpiece travel time measuring means measures a workpiece travel time in which a second acoustic wave travels through a portion of the workpiece to be inspected. An inspection distance determining means determines a distance through the workpiece traveled by the second acoustic wave from the workpiece travel time and the calibration acoustic velocity.

A primary advantage of the invention is that it accurately measures distances and dimensions of an inspected workpiece.

Another advantage of the invention is that it provides a real-time calibration which eliminates errors due to properties variations between and within a part.

Another advantage of the invention resides in the fact that measurements are corrected for variations in the elastic moduli and density which, in turn, may be a function of metallurgical composition and manufacturing process variations, and the like.

Yet another advantage of the invention is that tubular products and elongated workpieces having differing physical properties are inspected without manual recalibration and mechanical gauging.

Still further advantages of the present invention will become apparent to those skilled in the art upon a reading and understanding of the following detailed description.

BRIEF DESCRIPTION OF THE DRAWINGS

The invention may take form in various steps and arrangements of steps or in various parts and arrangements of parts, a preferred embodiment of which will be described in detail in this specification and illustrated in the accompanying drawings which form a part hereof and wherein.

DETAILED DESCRIPTION OF THE PREFERRED EMBODIMENT

Figure 1:
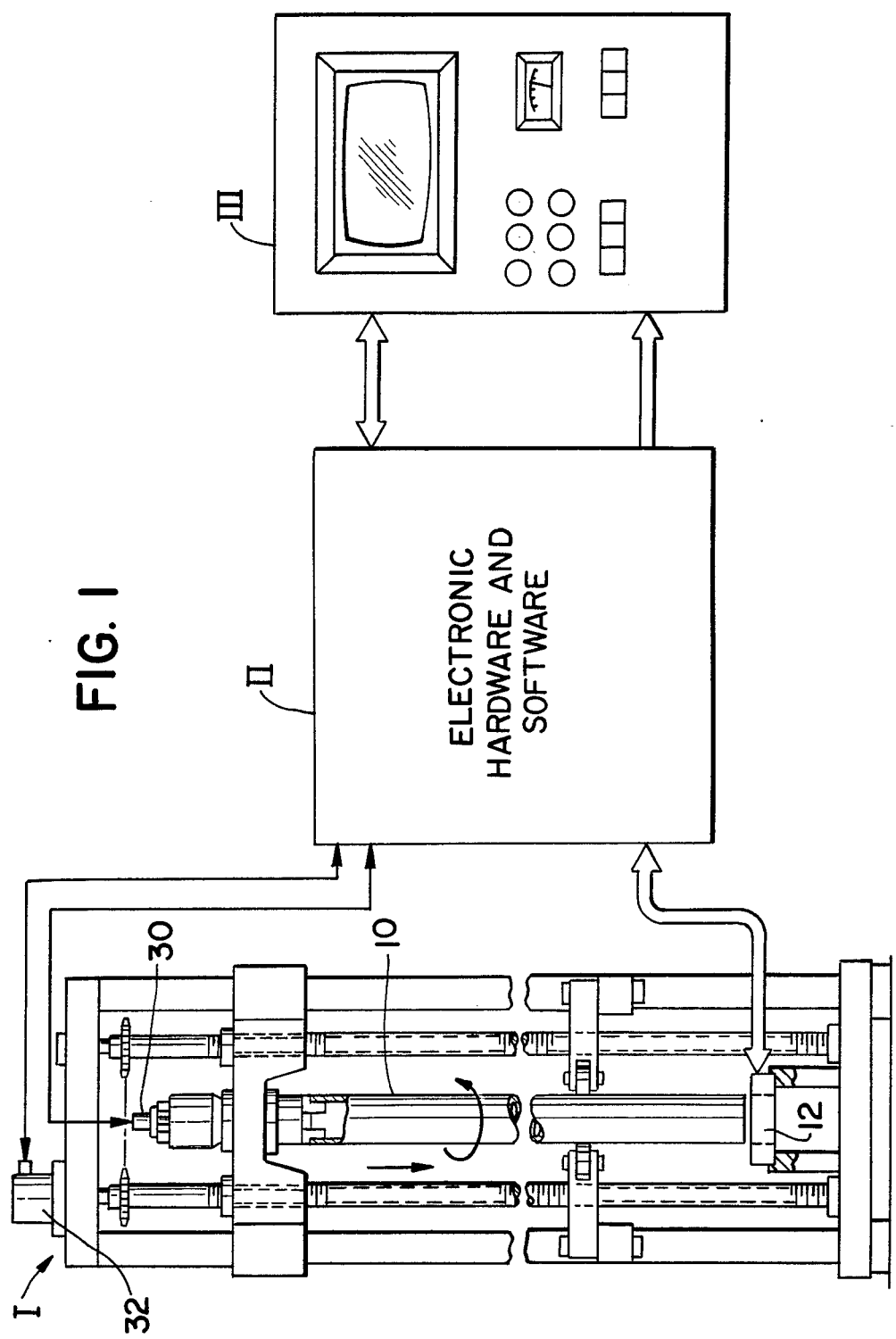
FIG. 1 is a somewhat diagrammatical view of an acoustic inspection system which practices the subject invention; and, FIGS. 2A and 2B are a two-part diagram illustrating electronic circuitry and software for implementing acoustic inspections in accordance with the invention.

Referring now to the drawings wherein the showings are for purposes of illustrating the preferred embodiment of the invention only and not for purposes of limiting same, FIG. 1 shows the acoustic inspection system as including a mechanical workpiece handling system I in which the workpiece is manipulated and illuminated with acoustic waves. Acoustic echoes, other acoustic properties, workpiece location and orientation, and the like are monitored in the mechanical system. An electronic hardware and software system II processes the data monitored by the workpiece handling system. From the monitored acoustic echoes, workpiece location and orientation, and the like, the electronic system determines selected physical distances and dimensions, such as thickness, location and depth of flaws, peripheral shape and the like. A display means III displays the determined inspection distances and other physical properties determined by the electronic system.

Figure 2A:
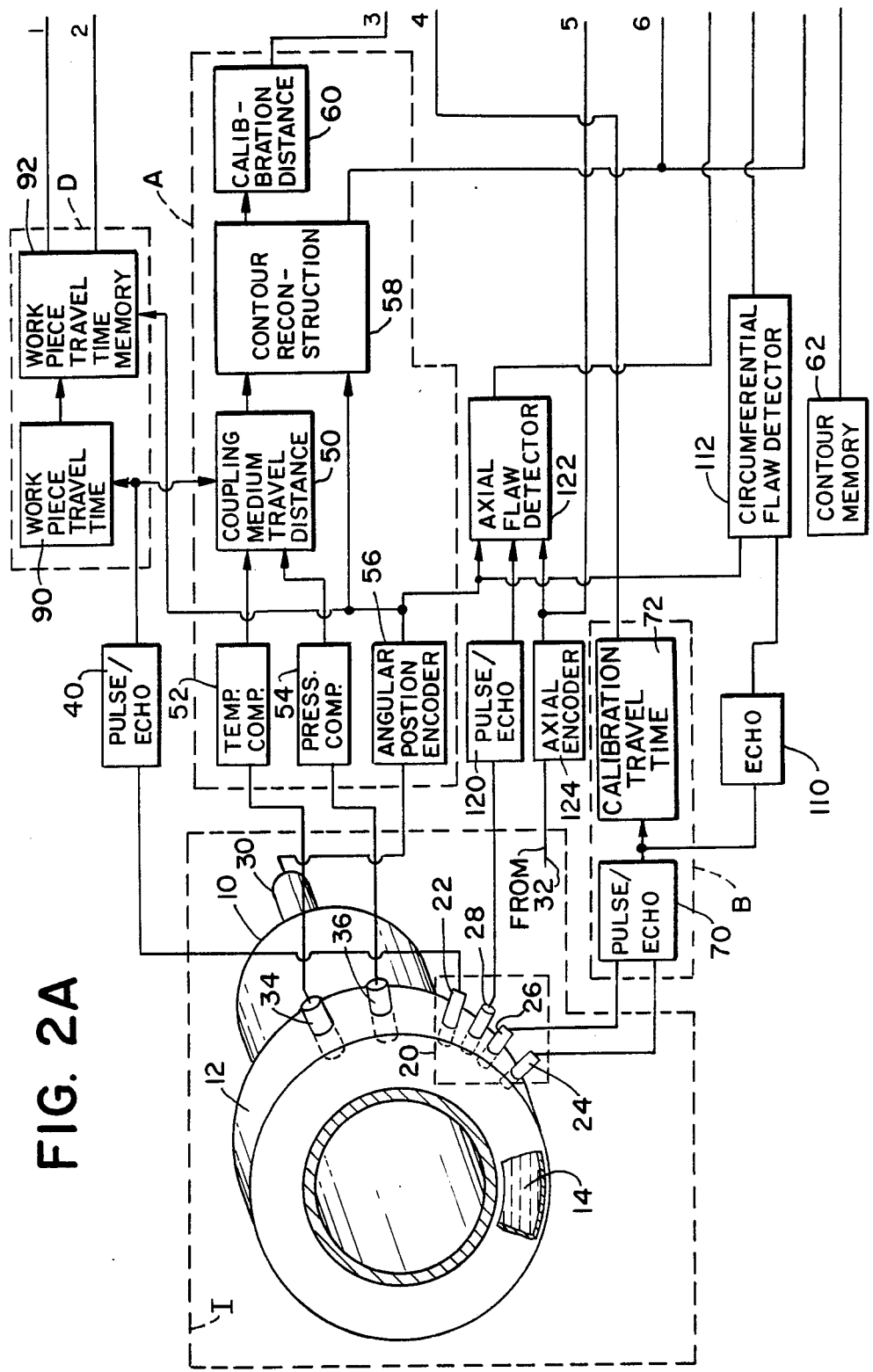
Figure 2B:
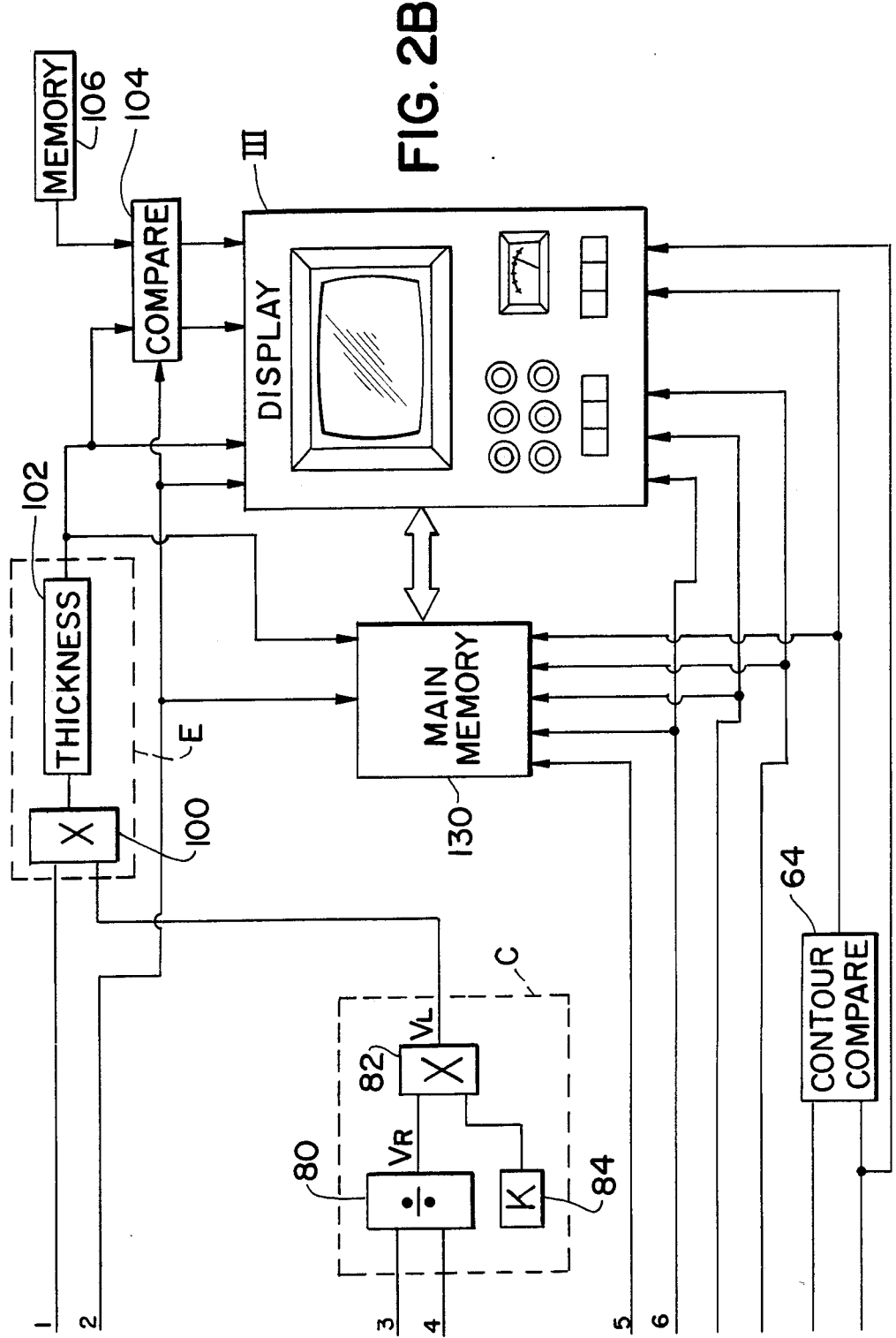

With reference to FIGS. 2A and 2B, the electronic system II includes a calibration distance determining means A which determines a preselected calibration distance along the inspected workpiece. In the preferred embodiment, the calibration distance comprises the workpiece circumference. A first or calibration travel time measuring means B measures a first or calibration travel time in which a first or Rayleigh acoustic wave travels the calibration distance. A calibration acoustic velocity determining means C determines a calibration acoustic velocity from the calibration distance and the first travel time. A second travel time measuring means D measures a second or workpiece travel time in which a second or longitudinal acoustic wave travels through a portion of the workpiece to be inspected. The acoustic velocities of the Rayleigh and longitudinal waves traveling through the same workpiece are related by a predetermined ratio. An inspection distance determining means E determines an inspection distance, such as thickness or distance from peripheral surface to a flaw, from the second travel time and the calibration acoustic velocity.

With reference to FIGS. 1 and 2A, the workpiece handling system I supports a workpiece, such as a length of tubular steel 10, for rotational and axial advancement through a coupling medium collar 12. The coupling medium collar 12 holds an acoustic coupling medium 14, such as water or other fluid substance in which the acoustic velocity of ultrasonic waves is known. The coupling medium is held in intimate, acoustically coupled contact with an outer or peripheral surface of the tubular workpiece 10. An acoustic transducer means 20 includes ultrasonic transducers 22, 24, 26, and 28 which extend through the coupling medium collar into acoustically coupled contact with the coupling medium. The ultrasonic transducers transmit acoustic waves through the coupling medium to the tubular workpiece and receive returning ultrasonic echoes.

The workpiece handling system I further includes rotational positioning means 30 for causing relative rotational movement between the workpiece and the ultrasonic transducers. The rotation brings different areas of the workpiece circumference into alignment with the transducer means 20 for acoustic examination. An axial advancement means 32 selectively advances the workpiece axially to enable additional portions of the workpiece to be acoustically examined. Acoustic coupling medium monitoring means, such as a temperature monitoring means 34 and a pressure monitoring means 36, monitor the acoustic coupling medium for variations in physical properties which would alter the acoustic velocity of acoustic waves traveling therethrough.

The calibration distance can be measured various ways. Mechanical gauging may be used for workpieces of some shapes. Alternately, laser gauging may be used successfully. In the preferred embodiment, however, the calibration distance is measured acoustically. Because the acoustic velocity in the workpiece is unknown, a direct acoustical measurement does not have sufficient accuracy for the present calibration purposes. Rather, the calibration distance is measured using the known acoustic velocity in the coupling medium to measure the calibration distance along the surface of the workpiece at the calibration medium-workpiece interface.

With reference to FIGS. 2A and 2B, the first or longitudinal wave ultrasonic transducer 22 is positioned radially to transmit longitudinal ultrasonic waves perpendicular to the surface of the workpiece. The longitudinal ultrasonic waves travel through the acoustic coupling medium with the predetermined coupling medium acoustic velocity. On reaching the coupling medium/workpiece interface, the acoustic wave is reflected in part and passes in part into the workpiece. The reflected acoustic wave or echo is received by the longitudinal wave ultrasonic transducer 22. A first pulse-echo means 40 controls the longitudinal wave ultrasonic transducer 22 to generate the ultrasonic waves and receives the ultrasonic echoes. The first pulse-echo means produces an output signal indicative of the time between transmission of the ultrasonic wave and receipt of each echo.

The calibration distance determining means A includes a coupling medium distance means 50 for converting the coupling medium travel time at the predetermined coupling medium acoustic velocity into a measurement of distance. A temperature compensation means 52 and a pressure compensation means 54 adjust the determined distance for variations in the temperature and pressure of the coupling medium. As the rotating means 30 causes the tubular workpiece and the longitudinal wave ultrasonic transducer 22 to undergo relative angular movement, an angular position encoder 56 produces position signals indicative of the relative angular position thereof. Each time the rotating means causes an incremental amount of relative rotation between the workpiece and first transducer, the first pulse-echo means 40 causes the longitudinal wave transducer to generate another ultrasonic wave and receive an ultrasonic echo.

The coupling medium distance means 50 determines the distance between the first transducer 22 and the surface of the workpiece. The relative rotational movement effectively moves the first transducer along a circular arc segment relative to the workpiece. The arc segment has a radius which is the same as the distance between the first transducer 22 and a central axis of the ultrasonic medium coupling collar 12. As the workpiece and first transducer undergo relative rotational movement, the distance between this defined circular arc segment and a corresponding portion of the outer surface of the workpiece is repeatedly measured. From the distances between the circular arc segment and the workpiece and from the rotational position signals, a contour reconstruction means 58 reconstructs the contour of the workpiece outer surface. A calibration distance calculation means 60 calculates the calibration distance from the reconstructed contour. If the contour is a circular arc or arc segment, which is the preferred peripheral contour of the tubing, the calibration distance is relatively easy to calculate. If the tubing is out-of-round, the calibration distance is determined by any conventional curve fitting technique such as approximating the workpiece surface with small incremental steps taken along the contour.

The contour reconstruction means 58 is connected with the display means III for displaying a representation of the reconstructed contour. Optionally, a contour memory 62 may store a preselected contour which denotes the desired or specification contour. The contour memory is connected with the display means such that the reconstructed and desired contours can be displayed side-by-side or superimposed to facilitate comparison. As yet another option, a contour comparing means 64 can be provided for electronically comparing the reconstructed and desired contours. The contour comparing means is operatively connected with the display means to display deviations between the reconstructed contour and the contour specifications.

The calibration travel time measuring means B includes a second pulse-echo control means 70 which operates ultrasonic transducers 24 and 26 to produce and detect a Rayleigh surface wave. The surface wave transducers generate a Rayleigh wave which travels the calibration distance circumferentially distance along the outer surface of the workpiece. In the preferred embodiment, the Rayleigh wave travels 360° around the circumference. Other, shorter arc lengths may be optionally used. A calibration travel time determining means 72 determines the travel time or duration which is required for the Rayleigh wave to travel the calibration distance.

The calibration acoustic velocity determining means C determines a calibration acoustic velocity. Particularly, a dividing means 80 divides the calibration distance, ie., the circumferential around the workpiece in the preferred embodiment, by the calibration travel time. This division of the distance by time produces a velocity, particularly the Rayleigh wave velocity, $V_R$. It is known that the ratio between the Rayleigh wave velocity and a shear wave velocity, $V_S$, is:

$$V_R = \frac{(0.87 + 1.12\sigma)}{1 + \sigma} V_S, \qquad (1)$$

where $\sigma$ is Poisson's ratio for the material. Further, it is known that the ratio between a shear wave, $V_S$, and a longitudinal wave, $V_L$, as generated by transducer 22, is:

$$V_L = \sqrt{\frac{2(1 - \sigma)}{1 - 2\sigma}} V_S \qquad (2)$$

Inserting Poisson's ratio and solving equations (1) and (2) for the longitudinal wave acoustic velocity in terms of the Rayleigh wave acoustic velocity, it can readily be seen that for steel tubular goods:

$$V_R = 2.09308 \, V_S \qquad (3)$$

Thus, the longitudinal wave acoustic velocity, ie., the velocity of the acoustic wave from the longitudinal wave transducer 22 traveling through the tubular workpiece, varies as a fixed ratio of the Rayleigh wave velocity. A multiplying means 82 multiplies the Rayleigh wave acoustic velocity by a preselected constant from a memory 84. The constant comprises the ratio between the Rayleigh wave and longitudinal wave velocities.

The workpiece travel time measuring means D includes a workpiece travel time determining means 90 which is operatively connected with the first pulse-echo control means 40. The workpiece travel time determining means 90 determines the travel time for the longitudinal ultrasonic wave from the longitudinal wave transducer 22 to travel through the workpiece. Specifically, the workpiece travel time means 90 determines the time for the longitudinal acoustic wave to travel from the outer surface to the inner surface which reflects the wave. The workpiece travel time determining means further determines the time for the longitudinal acoustic wave to travel from the outer surface to a flaw, if any, which reflects the longitudinal wave. Optionally, the workpiece travel time may be the travel time from the workpiece surface to the reflective interface and back to the surface. A workpiece travel time memory 92 receives the workpiece travel times as well as the angular position signals from the angular position encoder 56. The workpiece travel time memory stores each workpiece travel time in conjunction the corresponding angular position.

The inspection distance determining means E includes a multiplying means 100 which multiplies the workpiece travel time by the longitudinal acoustic velocity. The multiplication of time and velocity produces an indication of distance, particularly the distance between the inner and outer tubular workpiece surfaces and the distance between the outer workpiece surface and any acoustically reflective flaws. A thickness determining means 102 adjusts the distance signal from the multiplying means 100 to selected engineering units.

The display means III receives the tubular workpiece thickness from the thickness determining means 102 and the corresponding angular position from the workpiece travel time memory means 92. From this data, it produces a display indicative of the thickness of the pipe at each angular position around the circumference.

Optionally, a thickness comparing means 104 may compare the determined wall thicknesses from the thickness determining means 102 with preselected maximum and minimum thickness standards stored in a thickness memory means 106. The display means may display an indication of the location or coordinates at which the tubular workpiece has a thickness which is outside preselected specification. Alternately, all the thickness data may be displayed in either numerical or graphic form allowing the operator to make the decision as to whether or not the workpiece is satisfactory.

Because the acoustic wave is reflected back to the emitting ultrasonic transducer only by flaws which have a component perpendicular to the transducer, some flaws may not be detected by the longitudinal wave transducer 22. To this end, a Rayleigh wave echo detecting means 110 is connected with the second pulse-echo means 70. The Rayleigh wave echo detecting means detects any ultrasonic echoes received by the emitting Rayleigh wave transducer indicative of a circumferential flaw. A circumferential flaw detecting means 112 determines the position of the circumferential flaw on the circumference from the angular position signal and the time between the transmission of the Rayleigh wave and the receipt of the echo. The circumferential flaw detector 112 provides an output signal which is optionally displayed by the display means III.

Similarly, the fourth ultrasonic transducer 28 produces an axial, shear wave to detect the flaw components located transverse to the longitudinal axis of the workpiece. A third pulse-echo means 120 actuates and receives echoes from the shear wave transducer 28. An axial flaw detector 122 receives the shear wave pulse-echo signals, the angular position signals from the encoder 56, and axial position signals from an axial position encoder 124. From this data, the axial flaw detector determines the circumferential and axial position at which each axial flaw is detected for display by the display means III.

Optionally, a plurality of transducer means may be disposed at angular intervals around the coupling medium. Such means would be similar to transducer means 20 described in detail hereinabove. This enables acoustic data to be collected in parallel to increase the speed at which the tubular workpiece is inspected.

As yet another option, a main memory means 130 may be provided to store all or a selected part of the collected data. The main memory means may include tape or disc storage for storing a history of all inspected workpieces for future retrieval should an inspected workpiece fail.

In operation, a preselected physical calibration distance is determined. Specifically, the longitudinal wave transducer 22 generates a plurality of longitudinal wave pulses and receives a corresponding plurality of echoes as the transducer and workpiece undergo relative rotational movement. From the coupling medium travel times in which the longitudinal wave travels between the longitudinal wave transducer and the peripheral surface of the workpiece, the contour of the workpiece is reconstructed. From the contour of the workpiece, a preselected calibration distance is calculated. In the preferred embodiment, the calibration distance comprises the full circumference, although other distances may be employed satisfactorily if desired.

The travel time in which a calibration Rayleigh wave travels the calibration distance is then measured. Specifically, the Rayleigh wave transducer 24 generates an acoustic wave which causes a Rayleigh wave to travel around the circumference of the workpiece to the third transducer 26. A calibration or Rayleigh wave travel time is measured. The calibration distance is divided by the Rayleigh travel time to determine the Rayleigh wave velocity. The Rayleigh wave velocity is multiplied by a preselected constant which represents the Rayleigh wave to longitudinal wave velocity for determining the longitudinal wave velocity in the workpiece.

The travel times of the longitudinal waves from the first transducer through the workpiece are measured as the workpiece and first transducer undergo relative rotational movement. To expedite the calibration, the workpiece travel times are measured simultaneously with collecting the data to reconstruct the workpiece peripheral contour. Upon determining the longitudinal acoustic wave velocity, the stored workpiece travel times are thereafter converted into distances by multiplying the workpiece travel time by the longitudinal wave velocity.

The invention has been described with reference to the preferred embodiment. Obviously, modifications and alterations will occur to others upon a reading and understanding of the preceding detailed description of the preferred embodiment. It is intended to include all such modifications and alterations insofar as they come within the scope of the appended claims or the equivalents thereof.

Having thus described the invention, it is now claimed:

1. A method of acoustically inspecting a workpiece comprising:
    (a) determining a preselected physical calibration distance along a workpiece being inspected;
    (b) measuring a first travel time in which a first acoustic wave travels said calibration distance, said calibration distance being determined acoustically by measuring the travel times of acoustic waves through an acoustic coupling medium that contacts the workpiece along the calibration distance;
    (c) adjusting the determined distance for variations in the temperature and pressure of the coupling medium;
    (d) determining a calibration acoustic velocity from the calibration distance and the first travel time;
    (e) measuring a second workpiece travel time in which a second acoustic wave travels through a portion of the workpiece to be inspected; and,
    (f) determining an inspection distance through the workpiece traveled by the second acoustic wave from the calibration acoustic velocity and the second travel time.

2. The method as set forth in claim 1 further including repeating steps (a) through (f) to inspect another portion of the workpiece, whereby the calibration acoustic velocity is redetermined for each inspected workpiece portion.

3. The method as set forth in claim 1 wherein the calibration distance is determined along a first surface of the workpiece and the first acoustic wave comprises a Rayleigh wave which travels the calibration distance along the workpiece first surface.

4. The method as set forth in claim 3 wherein the second acoustic wave comprises a longitudinal wave which travels into the workpiece and produces at least one acoustic echo from at least one workpiece interface, such as a flaw and a second surface of the workpiece, said longitudinal wave traveling in the workpiece with a longitudinal wave velocity; and,
    wherein in the step of determining the calibration acoustic velocity, the longitudinal wave velocity is determined, whereby the inspection distance is indicative of at least one of the depth of a flaw in the workpiece and the thickness of the workpiece between the first and second surfaces.

5. The method as set forth in claim 4 wherein the step of determining the calibration acoustic velocity includes dividing the calibration distance by the first travel time to determine the acoustic velocity of the Rayleigh wave and multiplying the Rayleigh wave velocity by a preselected velocity constant which represents the ratio of the longitudinal wave velocity to the Rayleigh wave velocity, whereby the longitudinal wave acoustic velocity is determined.

6. The method as set forth in claim 4 wherein the step of determining the calibration distance includes:

transmitting the longitudinal wave from an ultrasonic transducer through an acoustic coupling medium to the workpiece, the longitudinal wave being in part reflected from the workpiece first surface producing a first longitudinal acoustic wave echo, the acoustic velocity of the longitudinal wave and echo in the coupling medium being predetermined;

measuring a plurality of coupling medium travel times, each coupling medium travel time being indicative of the time in which at least one of the longitudinal wave and echo travels through the acoustic coupling medium between a preselected surface and the workpiece first surface along the calibration distance; and, determining the calibration distance from the coupling medium travel times.

7. The method as set forth in claim 6 wherein the step of determining the calibration distance further includes determining the contour of the workpiece first surface at least along the calibration distance from the plurality of coupling medium travel times.

8. The method as set forth in claim 7 further including the step of comparing the determined first surface contour with a preselected contour, whereby conformity of the workpiece first surface contour to a preselected contour is determined.

9. The method as set forth in claim 8 wherein the step of measuring the plurality of coupling medium travel times further includes moving the workpiece and an ultrasonic transducer relative to each other as a plurality of longitudinal waves are generated and longitudinal echoes are received, measuring the second and coupling medium travel times, and storing the second travel times at least until sufficient coupling medium travel times are measured to determine the calibration distance and the longitudinal wave acoustic velocity.

10. An acoustic workpiece inspection system comprising:

a calibration distance determining means for determining a preselected physical calibration distance along a workpiece being inspected;

a first travel time measuring means for measuring a first travel time in which a first acoustic wave travels said calibration distance;

calibration acoustic velocity determining means for determining a calibration acoustic velocity from the calibration distance and the first travel time, the calibration acoustic velocity determining means being operatively connected with the calibration distance determining means and the first travel time measuring means;

a second travel time measuring means for measuring a second travel time in which a second acoustic wave travels through a portion of the workpiece to be inspected; and, inspection distance determining means for determining from the second travel time and the calibration acoustic velocity an inspection distance through the workpiece traveled by the second acoustic wave, the inspection distance determining means being operatively connected with the calibration acoustic velocity determining means and the second travel time measuring means.

11. The inspection system as set forth in claim 10 wherein the calibration distance determining means determines the calibration distance without mechanical contact with the workpiece.

12. The inspection system as set forth in claim 10 wherein the calibration distance determining means measures the calibration distance along a first surface of the workpiece and the first acoustic wave comprises a Rayleigh wave which travels the calibration distance along the first surface.

13. The inspection system as set forth in claim 12 wherein the second acoustic wave comprises a longitudinal wave which travels into the workpieces and produces at least one acoustic echo from at least one interface in the workpiece; and, wherein the calibration acoustic velocity determining means determines an acoustic velocity of the longitudinal wave.

14. The inspection system as set forth in claim 13 wherein the calibration acoustic velocity determining means includes a divider means for dividing the determined calibration distance by the first travel time to determine the Rayleigh wave velocity and first multiplying means for multiplying the Rayleigh wave velocity by a ratio of the longitudinal wave velocity to the Rayleigh wave velocity of the inspected workpiece.

15. The inspection system as set forth in claim 13 further including:

an acoustic coupling medium contacting at least a portion of the workpiece first surface including the calibration distance, the acoustic coupling medium transmitting acoustic waves with a known coupling medium velocity; and, wherein the calibration distance determining means includes: a coupling medium travel time measuring means for measuring a plurality of coupling medium travel times, each coupling medium travel time representing travel time of the longitudinal wave through the acoustic coupling medium between a preselected surface and the workpiece first surface along the calibration distance; and, wherein the calibration distance determining means determines the calibration distance from the coupling medium travel times.

16. The inspection system as set forth in claim 15 wherein the calibration distance determining means further includes means for determining the contour of the workpiece first surface at least along the calibration distance.

17. The inspection system as set forth in claim 16 further including contour comparing means for comparing the determined contour with a preselected contour.

18. The inspection system as set forth in claim 16 wherein the second and coupling medium travel time measuring means include at least one common ultrasonic transducer generating the longitudinal wave which travels through the coupling medium to the workpiece, echoes in part from the workpiece first surface and returns to the common ultrasonic transducer, in part enters and travels through the workpiece, and echoes in part from at least one interface, said echoes returning to the workpiece first surface and travel from the workpiece first surface through the coupling medium to the common ultrasonic transducer;

said system further including means for moving the workpiece and the common ultrasonic transducer relative to each other such that a plurality of second and coupling travel times are measured, each travel time corresponding to a predetermined position along the workpiece first surface; and, travel time storage means for storing at least the second travel times at least until sufficient coupling medium travel times are measured to determine the calibration distance and the calibration acoustic velocity.

19. An acoustic inspection apparatus for inspecting tubular workpieces in which velocities of ultrasonic inspection waves are unknown, the inspection apparatus comprising:

supporting means for supporting a tubular workpiece to be inspected;

an acoustic coupling medium operatively connected with the supporting means to be supported in contact with a first surface of the inspected workpiece, the acoustic coupling medium transmitting longitudinal ultrasonic waves with a predetermined coupling medium velocity;

at least one ultrasonic longitudinal wave transducer means for producing ultrasonic longitudinal waves and receiving ultrasonic longitudinal wave echoes, the transducer means being operatively connected with the supporting means in contact with the acoustic coupling medium and oriented to direct ultrasonic longitudinal waves radially toward the workpiece;

rotation means for causing relative rotational movement between the workpiece and the transducer means about a central axis of the workpiece, the rotation means producing a rotational position signal indicative of the relative angular orientation of the longitudinal wave transducer means and the workpiece;

a coupling medium travel time measuring means for measuring travel time of the ultrasonic longitudinal waves traveling between the transducer means and the workpiece first surface at a plurality of relative angular orientations between the workpiece and the longitudinal wave transducer means;

contour determining means for determining a contour of the workpiece first surface, the contour means being operatively connected with the rotation means to receive the rotational position signal therefrom and with the coupling medium travel time measuring means for receiving the measured coupling medium travel times therefrom;

calibration distance calculating means for calculating a calibration distance along the workpiece first surface from the contour, the calibration distance calculating means being operatively connected with the contour determining means;

at least one surface wave transducer means for producing ultrasonic Rayleigh waves traveling circumferentially along the workpiece first surface over the calibration distance, the surface wave transducer means being operatively connected with the supporting means in cotact with the acoustic coupling medium;

a surface wave travel time measuring means for measuring a surface wave travel time in which the Rayleigh wave traverses the calibration distance;

an acoustic velocity determining means for determining a longitudinal wave acoustic velocity in the workpiece, the acoustic velocity means being operatively connected with the calibration distance calculating means and the surface wave travel time measuring means;

a workpiece travel time measuring means for measuring workpiece travel times in which the longitudinal waves travel between the workpiece first surface and at least one workpiece interface such as an inner workpiece surface and a flaw, the workpiece travel time measuring means being operatively connected with the longitudinal wave transducer means; and, inspection distance determining means for determining a distance between the workpiece first surface and each interface, the inspection distance determining means being operatively connected with the acoustic velocity determining means and the workpiece travel time means.

* * * * *